US011305067B2

(12) United States Patent
Bar-El et al.

(10) Patent No.: US 11,305,067 B2
(45) Date of Patent: Apr. 19, 2022

(54) ACTIVATION BUTTON ASSEMBLY AND INJECTION NEEDLE INSERTION MECHANISM FOR INJECTOR

(71) Applicant: West Pharma. Services IL, Ltd., Ra'anana (IL)

(72) Inventors: Yossi Bar-El, Beit Arye (IL); Gil Yigal, Gan Yavne (IL)

(73) Assignee: West Pharma. Services IL, Ltd., Ra'anana (IL)

(*) Notice: Subject to any disclaimer, the term of this patent is extended or adjusted under 35 U.S.C. 154(b) by 129 days.

(21) Appl. No.: 16/637,375

(22) PCT Filed: Aug. 3, 2018

(86) PCT No.: PCT/US2018/045084
§ 371 (c)(1),
(2) Date: Feb. 7, 2020

(87) PCT Pub. No.: WO2019/032384
PCT Pub. Date: Feb. 14, 2019

(65) Prior Publication Data
US 2020/0179610 A1    Jun. 11, 2020

Related U.S. Application Data

(60) Provisional application No. 62/543,753, filed on Aug. 10, 2017.

(51) Int. Cl.
*A61M 5/315* (2006.01)
*A61M 5/31* (2006.01)
*A61M 5/32* (2006.01)

(52) U.S. Cl.
CPC ........ *A61M 5/3158* (2013.01); *A61M 5/3148* (2013.01); *A61M 5/3286* (2013.01); *A61M 2005/3115* (2013.01)

(58) Field of Classification Search
CPC .............. A61M 5/3158; A61M 5/3148; A61M 2005/3115; A61M 5/3287
See application file for complete search history.

(56) References Cited

U.S. PATENT DOCUMENTS 5,851,197 A    12/1998    Marano et al.
7,789,857 B2    9/2010    Moberg et al.
(Continued)

FOREIGN PATENT DOCUMENTS

JP    2002500525 A    1/2002
JP    5885667 B2    3/2016
(Continued)

OTHER PUBLICATIONS

Christoph Kapitza, M.D.; Basal-Prandial Insulin Delivery in Type 2 Diabetes Mellitusvia the V-Go™; Jan. 2008; Diabetes Tech. Society; vol. 2, Issue 1; (Year: 2008).*
(Continued)

*Primary Examiner* — Phillip A Gray
(74) *Attorney, Agent, or Firm* — BakerHostetler

(57) ABSTRACT

An injector includes an injection needle and an activation button assembly operatively connected to the injection needle. The activation button assembly is translatable from an unactuated position to an actuated position, the actuated position being visually different than the unactuated position. A position of the activation button assembly between the unactuated position thereof and the actuated position thereof defines a threshold point, and movement of the activation button assembly beyond the threshold point secures the activation button assembly in the actuated position, and drives the injection needle from a retracted position thereof to an injection position thereof.

20 Claims, 7 Drawing Sheets

(56) References Cited

U.S. PATENT DOCUMENTS

| | | |
|---|---|---|
| 2004/0002682 A1 | 1/2004 | Kovelman et al. |
| 2012/0143136 A1 | 6/2012 | Constantineau et al. |
| 2013/0226098 A1 | 8/2013 | Tokumoto et al. |

FOREIGN PATENT DOCUMENTS

| | | | |
|---|---|---|---|
| WO | 0202165 A2 | 1/2002 | |
| WO | 2012108955 A2 | 8/2012 | |
| WO | 2015164649 A1 | 10/2015 | |
| WO | 2017064483 A1 | 4/2017 | |
| WO | 2018060023 A1 | 4/2018 | |
| WO | WO-2018060023 A1 * | 4/2018 | ........ A61M 5/14248 |

OTHER PUBLICATIONS

International Preliminary Report on Patentability dated Aug. 12, 2019 in International Application No. PCT/US2018/045084.
International Search Report and Written Opinion dated Dec. 19, 2018 in International Application No. PCT/US2018/045084.
Office Action dated Jun. 2, 2021 in Japanese Application No. 2020-506901.

* cited by examiner

ACTIVATION BUTTON ASSEMBLY AND INJECTION NEEDLE INSERTION MECHANISM FOR INJECTOR

CROSS-REFERENCE TO RELATED APPLICATIONS

This application is a Section 371 of International Application No. PCT/US2018/045084, filed Aug. 3, 2018, which was published in the English language on Feb. 14, 2019, under International Publication No. WO 2019/032384 A1, which claims the benefit of priority under 35 U.S.C. § 119(e) U.S. Provisional Patent Application No. 62/543,753, titled "Tactile Button Feedback", filed on Aug. 10, 2017, the entire contents of each of which are incorporated herein by reference in their entirety.

BACKGROUND OF THE DISCLOSURE

The present disclosure is generally directed to an injector, and, more particularly, to an activation button and an injection needle insertion mechanism of an injector.

An injector, such as, for example, a drug injector, is often self-operated by a user unfamiliar with the device. Accordingly, the user may mishandle or improperly use the injector absent sufficient guidance and feedback. For example, a user may fail to properly activate the injector if unsure of the status of the device, or may prematurely interrupt the injection process. A user may also be confused whether they properly actuated an activation button. Alternatively, a user may be confused whether the device has been previously used or is still new. Such scenarios may result in improper use of the device, potentially dangerous or wasteful premature removal of the device, unnecessary disposal of the device, and/or at least anxiety on the part of the user. Moreover, improper activation of the injector may result in incomplete injection needle deployment.

Therefore, it would be advantageous to manufacture an injector having an activation button with both visual and tactile, e.g., haptic, differentiation between an unactuated state and a properly actuated state thereof to clearly and intuitively indicate proper activation to the user. It would also be advantageous to manufacture an injector employing a needle insertion mechanism that is deployed solely upon proper activation of the device, thereby removing user induced error in deployment.

BRIEF SUMMARY OF THE DISCLOSURE

Briefly stated, one aspect of the present disclosure is directed to an injector. The injector includes an injector housing, and an injection needle translatable along a needle axis between a retracted position, wherein at least a tip of the injection needle is contained within the injector housing, and an injection position, wherein at least the tip of the injection needle protrudes from the injector housing. An activation button assembly is movably mounted to the injector housing and operatively connected to the injection needle. The activation button assembly is translatable along a button axis, parallel to the needle axis, from an unactuated position to an actuated position, the actuated position being visually different than the unactuated position. A biasing member is connected with the activation button assembly and the injection needle. The biasing member is stabilized in a stored energy state in the unactuated position of the activation button assembly, and released in the actuated position of the activation button assembly into an energy releasing state to drive the injection needle along the needle axis from the retracted position thereof to the injection position thereof. A position of the activation button assembly between the unactuated position thereof and the actuated position thereof defines a threshold point, and movement of the activation button assembly beyond the threshold point secures the activation button assembly in the actuated position.

Another aspect of the invention is directed to an injector. The injector includes an injector housing, and an injection needle translatable along a needle axis between a retracted position, wherein at least a tip of the injection needle is contained within the injector housing, and an injection position, wherein at least the tip of the injection needle protrudes from the injector housing. An activation button assembly is movably mounted to the injector housing and operatively connected to the injection needle. The activation button assembly is translatable along a button axis, parallel to the needle axis, from an unactuated position to an actuated position, the actuated position being visually different than the unactuated position. A biasing member is connected with the activation button assembly and the injection needle. The biasing member is stabilized in a stored energy state in the unactuated position of the activation button assembly, and released in the actuated position of the activation button assembly into an energy releasing state to drive the injection needle along the needle axis from the retracted position thereof to the injection position thereof. A position of the activation button assembly between the unactuated position thereof and the actuated position thereof defines a threshold point, and release of the biasing member into the energy releasing state to drive the injection needle from the retracted position thereof to the injection position thereof is triggered solely upon movement of the activation button assembly beyond the threshold point.

BRIEF DESCRIPTION OF THE DRAWINGS

The following detailed description of aspects of the disclosure will be better understood when read in conjunction with the appended drawings. It should be understood, however, that the disclosure is not limited to the precise arrangements and instrumentalities shown. In the drawings.

DETAILED DESCRIPTION OF THE DISCLOSURE

Figure 1:
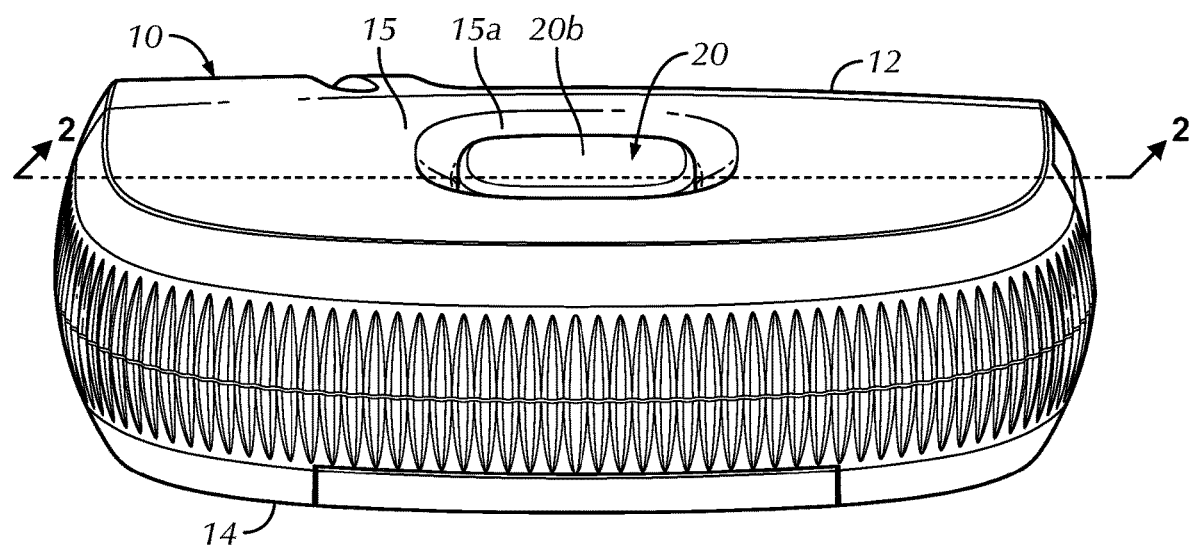
FIG. 1 is a top and front perspective view of a wearable injector, in accordance with a first embodiment of the present disclosure.

Certain terminology is used in the following description for convenience only and is not limiting. The words "lower," "bottom," "upper" and "top" designate directions in the drawings to which reference is made. The words "inwardly," "outwardly," "upwardly" and "downwardly" refer to directions toward and away from, respectively, the geometric center of the injector, and designated parts thereof, in accordance with the present disclosure. Unless specifically set forth herein, the terms "a," "an" and "the" are not limited to one element, but instead should be read as meaning "at least one." The terminology includes the words noted above, derivatives thereof and words of similar import.

It should also be understood that the terms "about," "approximately," "generally," "substantially" and like terms, used herein when referring to a dimension or characteristic of a component of the disclosure, indicate that the described dimension/characteristic is not a strict boundary or parameter and does not exclude minor variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Referring to the drawings in detail, wherein like numerals indicate like elements throughout, there is shown in FIGS. 1-5 an injector, generally designated 10, in accordance with a first embodiment of the present disclosure. In the illustrated embodiment, the injector 10 takes the form of a wearable injector (patch injector), such as, for example, without limitation, a wearable drug injector, but the disclosure is not so limited. As should be understood by those of ordinary skill in the art, the injector 10 generally includes a housing 12 having a first surface 14 configured to contact a skin surface of a user (not shown), e.g., a patient, the first surface 14 having an opening 14a therein. In the illustrated embodiment, the first surface 14 defines a base surface of the injector housing 12, but the disclosure is not so limited. The housing 12 also includes a second surface 15 opposing the first surface 14. In the illustrated embodiment, the second surface 15 defines a top, external surface of the injector housing 12, but the disclosure is not so limited.

As shown in FIGS. 2-5, a needle hub 16, constructed, for example, from a polymeric or metal material, combinations thereof, or the like, is movably mounted within the injector housing 12 and an injection needle 18 is supported by the movable needle hub 16 in a manner well understood by those of ordinary skill in the art. In the illustrated embodiment, the needle hub 16 and the injection needle 18 are axially translatable along a needle axis A (FIG. 2) extending substantially perpendicularly to the first surface 14, between a retracted position (FIG. 2), wherein at least a tip 18a of the injection needle 18 is contained within the injector housing 12, and an injection position (FIG. 5), wherein at least the tip 18a of the injection needle 18 protrudes from the injector housing 12 through the opening 14a. As should be understood by those of ordinary skill in the art, however, the axis A may be positioned at angles other than 90° relative to the first surface 14. As also should be understood, the injection needle 18 may be movably mounted within the injector housing 12 via other mechanisms than the needle hub 16.

A depressible activation button assembly 20, constructed, for example, from a polymeric or metal material, a combination thereof, or the like, is movably mounted to the injector housing 12 and operatively connected to the injection needle 18 (as will be explained in further detail). In the illustrated embodiment, the activation button assembly 20 is positioned within a cradle indent 15a in the second surface 15 of the injector housing 12, but the disclosure is not so limited. The cradle indent 15a defines an opening in the second surface 15, through which the activation button assembly 20 extends into the interior of the injector housing 12. The activation button assembly 20 is translatable along a button axis B, parallel to the needle axis A, from an unactuated position (FIGS. 1, 2) to an actuated position (FIG. 5) (as will be explained in further detail below). In the illustrated embodiment, the injector housing 12 includes a securing post 12a (shown best in FIGS. 2, 5) projecting upwardly from the first surface 14 toward the second surface 15 along the button axis B. The securing post 12a slidably receives a complementary translation post 20a (shown best in FIGS. 2, 5) projecting downwardly from the activation button assembly 20 along the button axis B. The translation post 20a is configured, i.e., shaped and dimensioned, to matingly slide within the securing post 12a during translation of the activation button assembly 20 with respect to the injector housing 12 to assist in stabilizing translation of the activation button assembly 20 along the button axis B.

As shown in FIGS. 2-5, a biasing member 22 is operatively connected with the activation button assembly 20 and the injection needle 18. The biasing member 22 is stabilized in a stored energy state in the unactuated position of the activation button assembly 20 (FIG. 2) and released in the actuated position (FIG. 5) of the activation button assembly 20 into an energy releasing state to drive the injection needle 18 along the needle axis A from the retracted position thereof to the injection position thereof. As should be understood by those of ordinary skill in the art, the stored energy state of the biasing member 22 is a state in which the biasing member 22 stores at least some potential energy. The energy releasing state of the biasing member 22 is a state of the biasing member 22 in which the biasing member 22 releases at least some of the stored potential energy from the stored energy state.

In the illustrated embodiment, the biasing member 22 takes the form of a coil spring expandable from the energy storing state, in which the spring 22 is at least partially compressed, to the energy releasing state, in which the spring 22 is expanded relative to the energy storing state. As should be understood by those of ordinary skill in the art, however, the biasing member 22 may alternatively take the form of other members capable of storing and releasing energy. Non-limiting examples include other springs (e.g., torsion or leaf springs), elastic bands, and the like. Alternatively, the biasing member 22 may take the form of an actuator configured to apply a translational force onto the injection needle 18.

In the illustrated embodiment, the coil spring 22 is mounted between the needle hub 16 and the activation button assembly 20, i.e., the spring 22 abuts the activation button assembly 20 at one end and abuts the needle hub 16 at an opposing end. In the energy storing state thereof, the spring 22 applies a biasing force at the one end on the activation button assembly 20, biasing the activation button assembly 20 into the unactuated position thereof, and also applies an oppositely directed biasing force at the other end on the needle hub 16.

Figure 2:
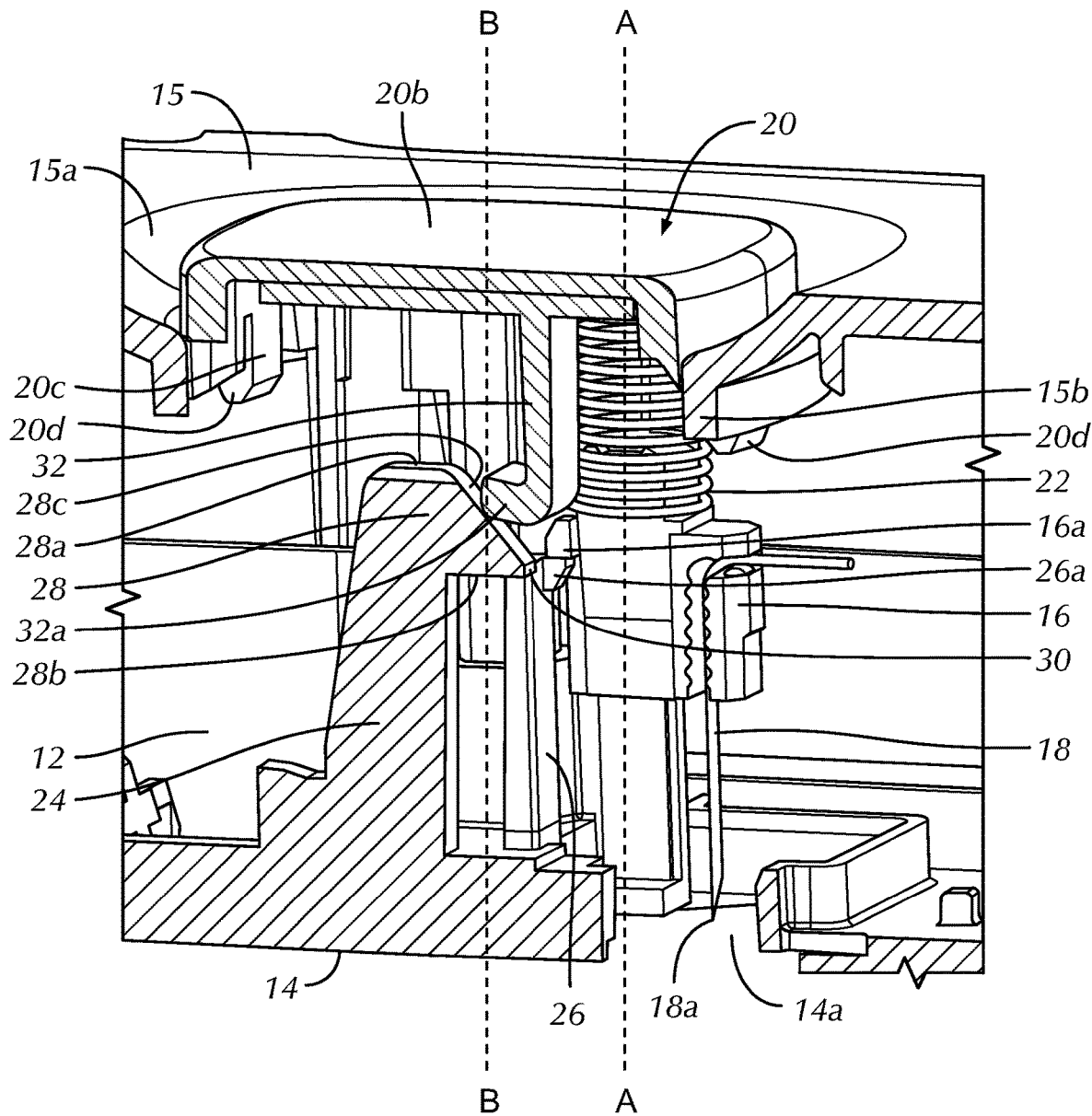
FIG. 2 is an enlarged partial cross-sectional view of an activation button assembly and an injection needle insertion mechanism of the injector of FIG. 1, taken along the sectional line 2-2 of FIG. 1, with the activation button assembly in an unactuated position thereof and the injection needle in a retracted position thereof.

As shown best in FIG. 2, the activation button assembly 20 defines an external surface 20b, e.g., the top surface of the button assembly 20 engageable by a user, and a plurality of angularly spaced members 20c extending therefrom and forming respective hook shaped terminal ends 20d. The members 20c may be integral, i.e., unitary and monolithic, with the surface 20b, but the disclosure is not so limited. The cradle indent 15a, within which the activation button assembly 20 is positioned, includes a flanged member 15b extending downwardly therefrom. In the unactuated position of the activation button assembly 20 (FIG. 2), the hook shaped terminal ends 20d of the members 20c engage the flanged member 15b under the biasing force of the spring 22, thereby maintaining the activation button assembly 20 in the unactuated position and preventing the activation button assembly 20 from being removed from the housing 12. As should be understood by those of ordinary skill in the art, however, the activation button assembly 20 may be secured in the unactuated position thereof via other means, currently known or that later become known. In the unactuated position, the external surface 20b of the activation button assembly 20 is substantially flush with the second surface 15 of the injector housing 12 (FIG. 2). As will be explained in further detail below, the activation button assembly 20 is depressed within the cradle indent 15a in the actuated position relative to the unactuated position (FIG. 5), e.g., the external surface 20b is below the second surface 15a. As also should be understood, however, the activation button assembly 20 may alternatively be positioned differently relative to the injector housing 12 in the actuated and unactuated positions thereof, wherein the actuated position of the activation button assembly 20 remains visually different than the unactuated position thereof. For example, the activation button assembly 20 may be elevated relative to the second surface 15 in the unactuated position thereof. Advantageously, the visual and haptic differentiation between the activation button assembly 20 positions serves as an intuitive, noticeable and continuous indication for the user that the injector has been successfully activated and remains activated.

The opposite end of the spring 22, as indicated previously, abuts the needle hub 16 and applies a biasing force onto the needle hub 16 directed toward the first surface 14, along the needle axis A. The spring 22 is prevented from driving the needle hub 16 and the injection needle 18 into the injection position, however, until the activation button assembly 20 is moved into the actuated position, as will be explained further below.

Figure 3:
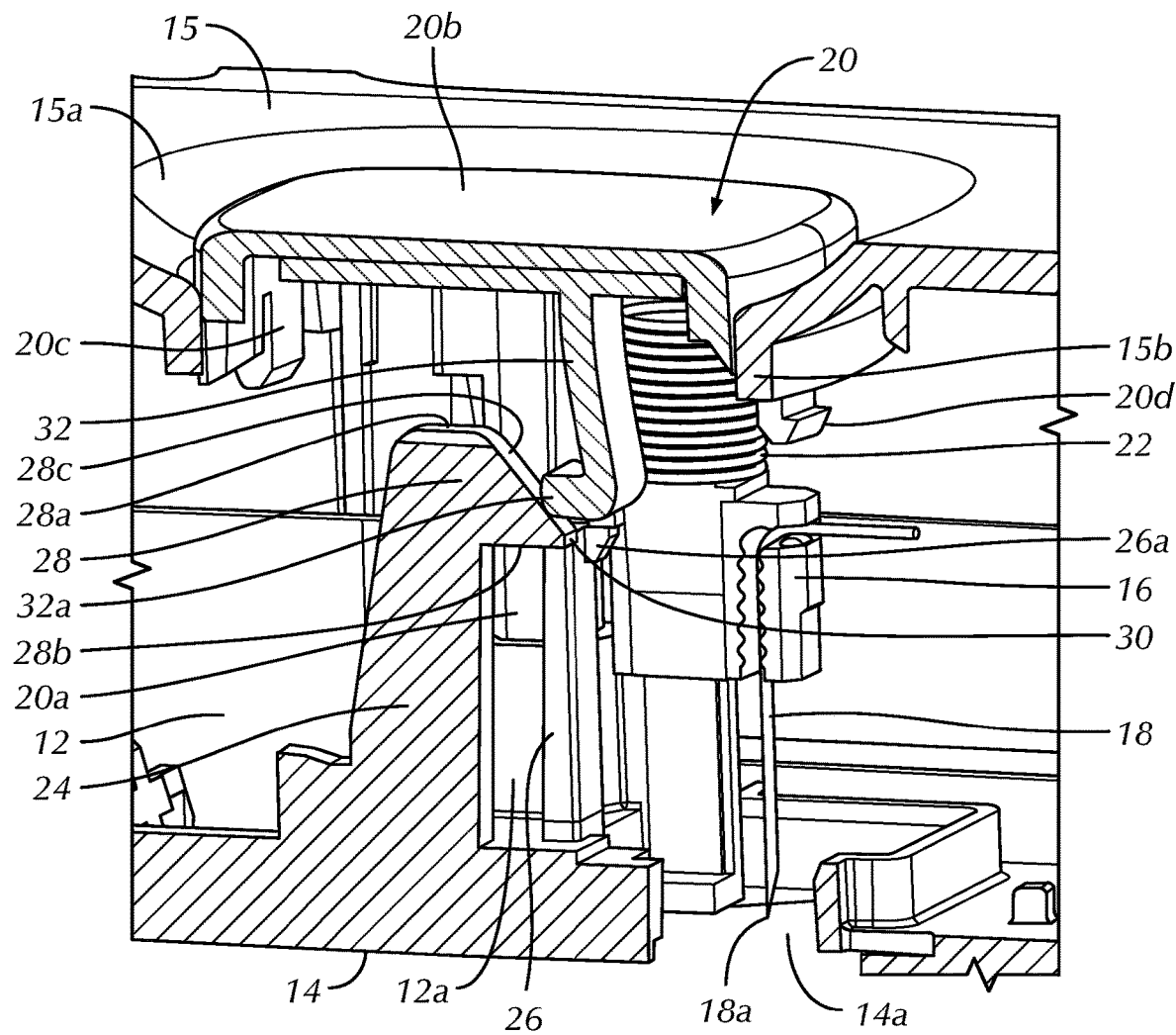
FIG. 3 is an enlarged partial cross-sectional view of the activation button assembly and the injection needle insertion mechanism of the injector of FIG. 1, taken along the sectional line 2-2 of FIG. 1, with the activation button assembly moved toward an actuated position thereof and the injection needle in the retracted position thereof.
Figure 4:
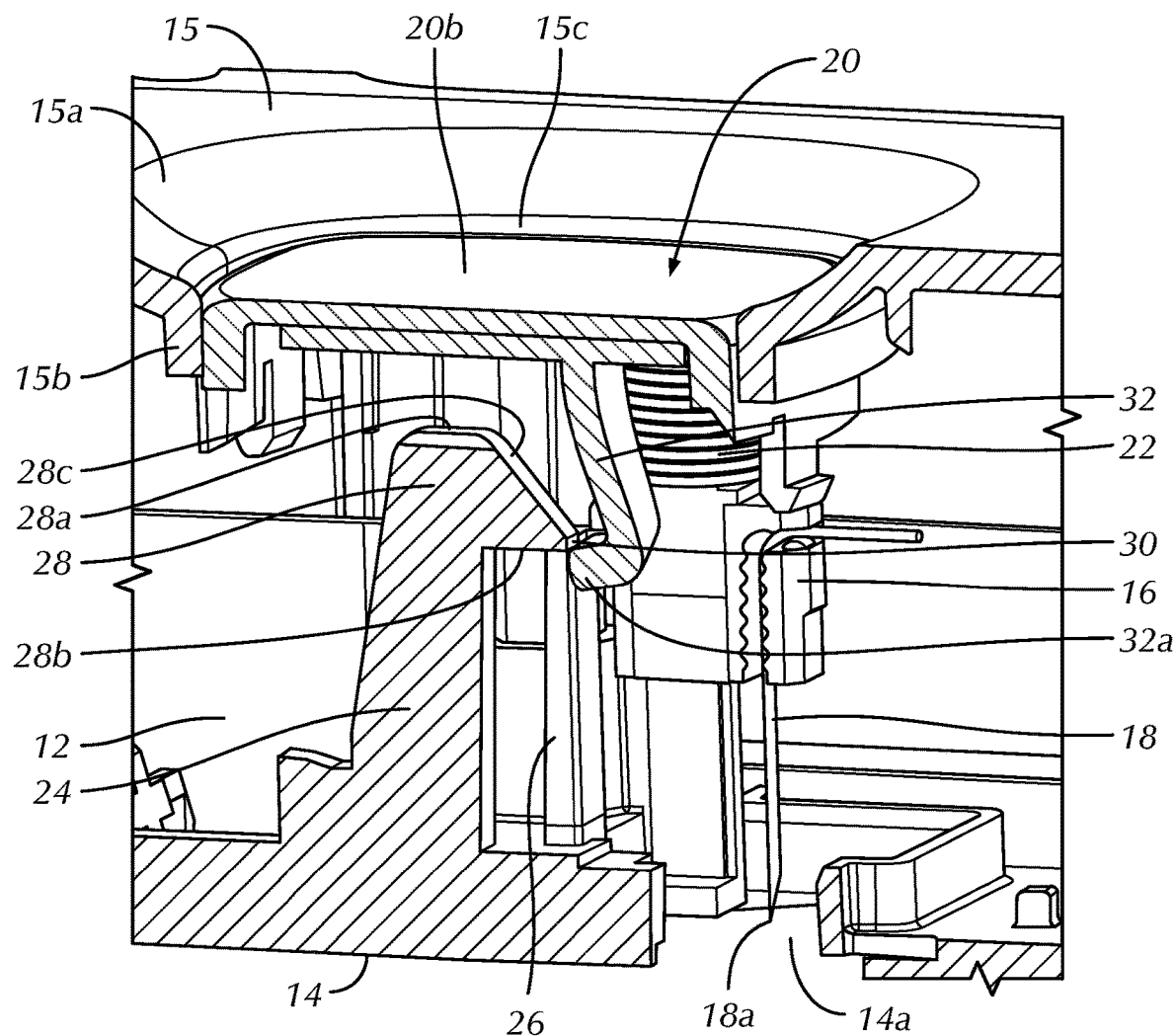
FIG. 4 is an enlarged partial cross-sectional view of the activation button assembly and the injection needle insertion mechanism of the injector of FIG. 1, taken along the sectional line 2-2 of FIG. 1, with the activation button assembly further moved toward the actuated position thereof and the injection needle in the retracted position thereof.

In the illustrated embodiment, as shown in FIGS. 2-4, the injector 10 includes an elongate first post 24 connected with the injector housing 12 and projecting upwardly therefrom, and a deflectable, second post 26 connected with the injector housing 12 and projecting upwardly therefrom. The first and second posts 24, 26 may be integral, i.e., unitary and monolithic, with the injector housing 12, but the disclosure is not so limited. The first and second posts 24, 26 may also each be constructed from a polymeric or metal material, combinations thereof, or the like. In the illustrated embodiment, the first and second posts, 24, 26 project upwardly from the first surface 14, but the disclosure is also not so limited, and the first and second posts 24, 26 may project from other portions of the injector housing 12. As shown best in FIGS. 2-3, the second post 26 includes a flange 26a projecting laterally therefrom. In the illustrated embodiment, the flange 26a projects laterally from a terminal, upper end of the second post 26, but the disclosure is not so limited. As should be understood, the flange 26a may project laterally from others portions of the second post 26, provided that the flange 26a is capable of performing the functions described herein. The flange 26a supports a portion of the needle hub 16 thereon, thereby securing the needle hub 16 and the injection needle 18 in the retracted position thereof, i.e., obstructing the spring 22 from driving the needle hub 16 and the injection needle 18 into the injection position. In the illustrated embodiment, the needle hub 16 includes a complementary laterally extending flange 16a abutting the flange 26a, but the disclosure is not so limited. As should be understood, however, others portions of the needle hub 16 may engage the flange 26a, such as, for example, without limitation, an underside of the needle hub 16. Accordingly, engagement of the hook shaped terminal ends 20d of the members 20c with the flanged member 15b of the cradle indent 15a at one end of the spring 22, and engagement of the flange 26a of the second post 26 with the flange 16a of the needle hub 16 maintain the spring 22 in an energy storing state, prior to movement of the activation button assembly 20 into the actuated position thereof.

The elongate first post 24 includes a terminal upper end defining a flange 28. The flange 28 includes an upper surface 28a, defining the upper end of the first post 24, a lower surface 28b projecting laterally from the first post 24 further than a lateral extent of the upper surface 28a, and a downwardly inclined surface 28c from the upper surface 28a to the lower surface 28b. The lateral projection of the lower surface 28b from the elongate post 24 defines an undercut underlying the inclined surface 28c. The inclined surface 28c and lower surface 28b, i.e., the undercut, of the elongate first post 24 meet at a vertex 30.

The activation button assembly 20 includes a first arm 32 projecting downwardly from the top surface 20b. The first arm 32 may be integral, i.e., unitary and monolithic, with the top surface 20b, but the disclosure is not so limited. Alternatively, for example, the first arm 32 may be attached to the activation button assembly 20 via other attachment means currently known or that later become known. The first arm 32 may also be constructed from a polymeric or metal material, combinations thereof, or the like. The first arm 32 includes a laterally projecting, flanged, terminal, lower end 32a, forming a generally hook-shaped end 32a of the first arm 32. The flange 32a is positioned opposite the downwardly inclined surface 28c of the first post 24 in the unactuated position of the activation button assembly 20. In one embodiment, a lateral tip of the flange 32a may define a complementary incline to the inclined surface 28c for smoother sliding thereon. As should be understood by those of ordinary skill in the art, the position of the flange 28 along the first post 24 and the position of the flange 32a along the first arm 32 is not limited to the respective upper and lower ends of the first post 24 and the first arm 32, but rather may be moved so long as the flange 32a is positioned opposite the downwardly inclined surface 28c.

The first arm 32 is constructed to be more elastically flexible than the elongate first post 24, and the second post 26 is constructed to be more elastically flexible than the first arm 32. That is, the first post 24 is constructed to define a greater bending stiffness, i.e., resistance against bending deformation, than the first arm 32, and the first arm 32 is constructed to define a greater bending stiffness than the second post 26. Such properties may be achieved via relative material properties, between the first post 24, the first arm 32 and the second post 26, relative dimensions between the first post 24, the first arm 32 and the second post 26, or a combination thereof.

As shown in FIGS. 2-5, depression of the activation button assembly 20 along the button axis B engages the flange 32a of the first arm 32 with the inclined surface 28c of the first post 24 and slides the flange 32a down the inclined surface 28c. As the first arm 32 is more elastically flexible, i.e., deflectable, than the first post 24, sliding of the flange 32a along the inclined surface 28c elastically deflects the first arm 32 (FIGS. 3, 4) from an original state, e.g., undeflected or less deflected, thereof (FIG. 2).

The vertex 30 defines a threshold point along the activation button assembly 20 pathway, and solely movement of the activation button assembly 20 beyond the vertex 30 secures the activation button assembly in the actuated position thereof. That is, movement of the first arm 32 of the activation button assembly 20 beyond the vertex 30 (FIG. 5) triggers retraction of the deflected first arm 32 back toward the original state thereof, and the flanged terminal end 32a thereof engages with the undercut 28b of the elongate first post 24, e.g., hooks or snaps back into engagement with the undercut 28b, to secure the activation button assembly in the actuated position thereof. Alternatively, movement of the activation button assembly 20 that does not position the flange 32a beyond the vertex 30 (e.g., FIG. 3) results in return of the activation button assembly 20 to the unactuated position thereof. That is, depression of the activation button assembly 20 further compresses the spring 22 in the energy storing state thereof, thereby charging the spring 22 with additional potential energy, until the flange 32a extends beyond the vertex 30. Accordingly, movement of the activation button assembly 20 that does not extend the flange 32a beyond the vertex 30 results in the spring 22 driving the activation button assembly 20 back toward the unactuated position. Additionally, or alternatively, the elasticity of the deflected first arm 32 drives the first arm 32 back up the inclined surface 28c to return to original state thereof, thereby returning the activation button assembly 20 to the unactuated position thereof.

Figure 5:
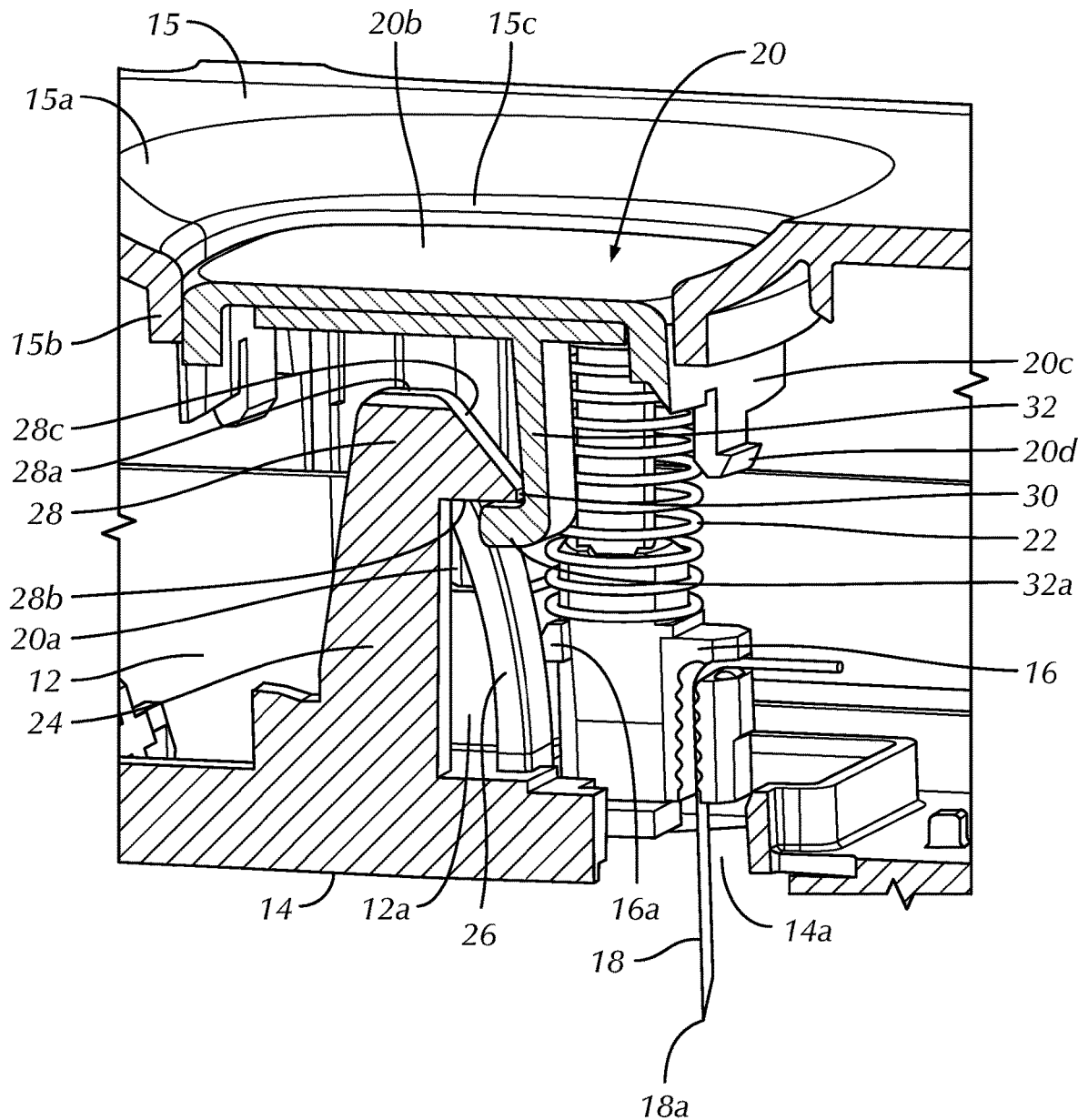
FIG. 5 is an enlarged partial cross-sectional view of the activation button assembly and the injection needle insertion mechanism of the injector of FIG. 1, taken along the sectional line 2-2 of FIG. 1, with the activation button assembly in the actuated position thereof and the injection needle in an injection position thereof.

Movement of the flange 32a of the first arm 32 beyond the vertex 30 of the first post 24, thereby triggering retraction of the deflected first arm 32 back toward the original, e.g., undeflected or less deflected, state thereof allows the flange 32a of the first arm 32 to engage with and deflect the second post 26 (due to the previously disclosed relative properties thereof) in the opposite direction. That is, the second post 26 is positioned such that return of the first arm 32 toward the original state thereof allows the first arm 32 to contact and deflect the second post 26. Accordingly, deflection of the second post 26 moves the flange 26a of the deflected second post 26 away from the flange 16a of the needle hub 16, thereby releasing the needle hub 16, and, in turn, releasing the spring 22 into the energy releasing state to drive the needle hub 16 and the injection needle 18 from the retracted position thereof to the injection position thereof (FIG. 5). Thus, release of the spring 22 into the energy releasing state thereof is triggered upon movement of the first arm 32 of the activation button assembly 20 beyond the vertex 30, i.e., the threshold point.

Advantageously, therefore, insufficient user depression of the activation button assembly 20 that does not move the first arm 32 of the activation button assembly 20 beyond the threshold point 30 will merely return the injector 20 into the original unused state thereof, without any negative affect on injection needle 18 deployment. Further advantageously, once the first arm 32 moves beyond the threshold point, the injection needle 18 is driven into the injection position thereof under the biasing force of the biasing member 22, irrespective of the force utilized to depress the activation button assembly 20. Thus, a desired preset injection force of the injection needle 18 may be configured during injector manufacture, according to the biasing force of the biasing member 22.

Figure 6:
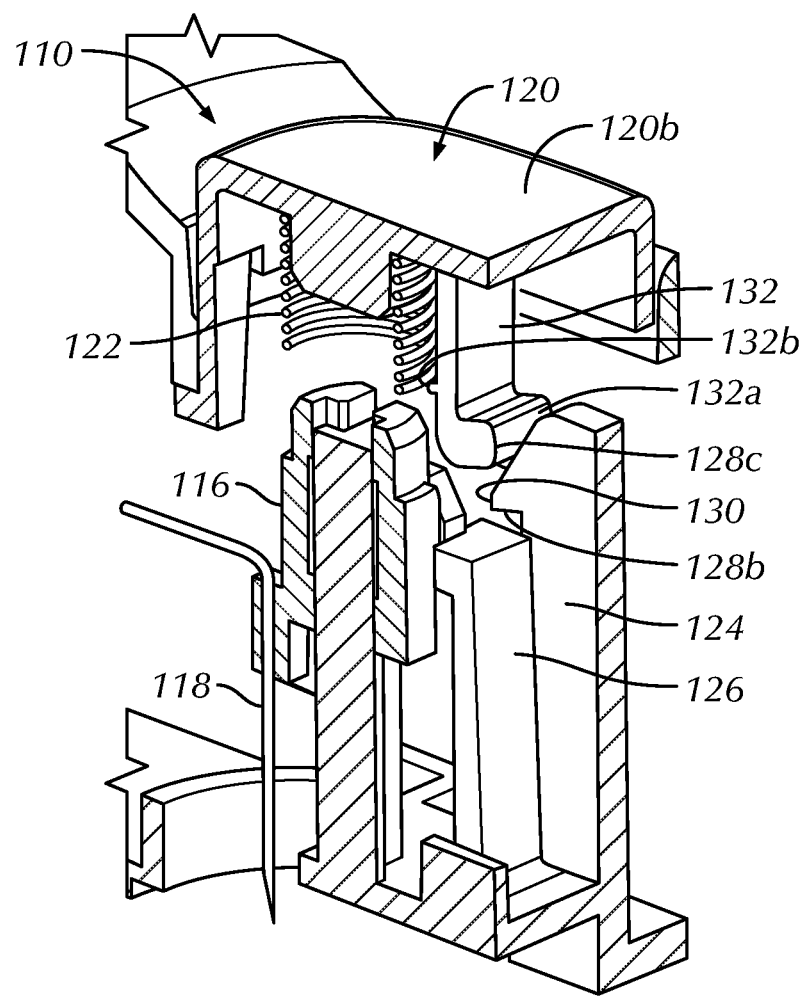
FIG. 6 is an enlarged, partial cross-sectional view of the activation button assembly and the injection needle insertion mechanism in accordance with a second embodiment of the present disclosure, taken along the sectional line 2-2 of FIG. 1, with the activation button assembly in the unactuated position thereof and the injection needle in the retracted position thereof.
Figure 7:
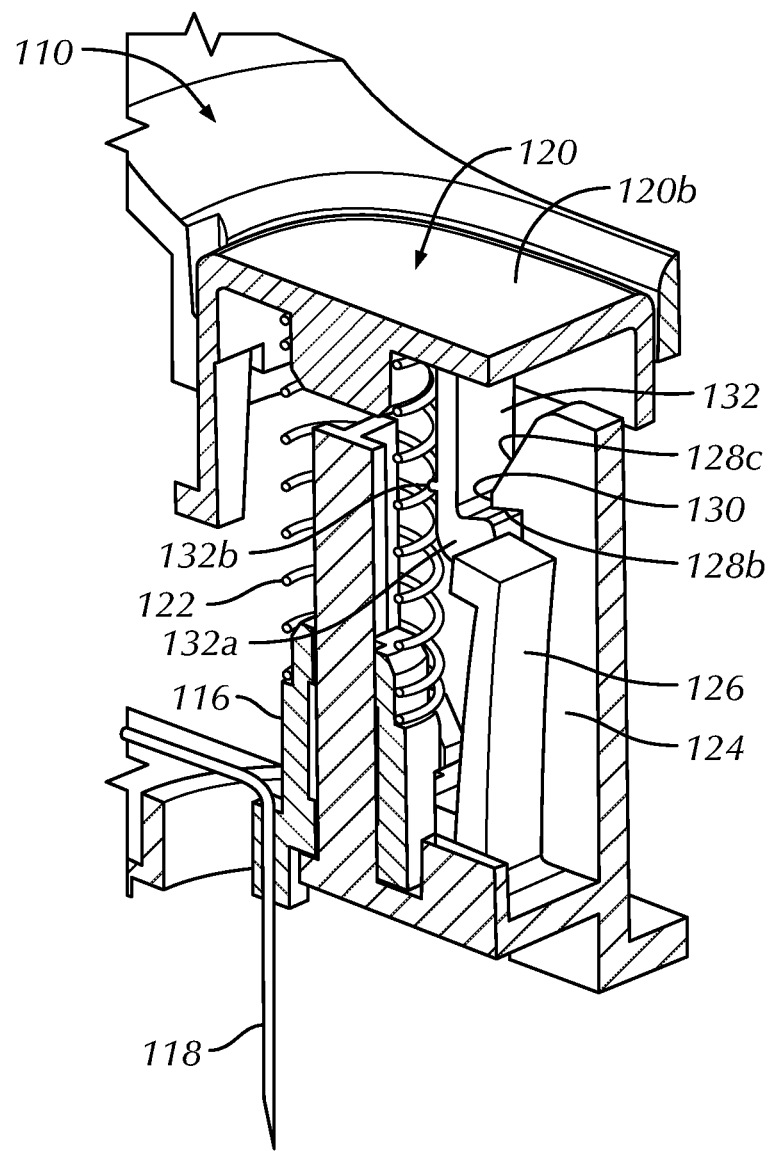
FIG. 7 is an enlarged, partial cross-sectional view of the activation button assembly and the injection needle insertion mechanism of FIG. 6, taken along the sectional line 2-2 of FIG. 1, with the activation button assembly in the actuated position thereof and the injection needle in the injection position thereof.

FIGS. 6-7 illustrate a second embodiment of the injector 110. The reference numerals of the second embodiment are distinguishable from those of the above-described first embodiment (FIGS. 1-5) by a factor of one-hundred (100), but otherwise indicate the same elements as indicated above, except as otherwise specified. The injector 110 of the present embodiment is substantially similar to that of the earlier embodiment. Therefore, the description of certain similarities and modes of operation between the embodiments may be omitted herein for the sake of brevity and convenience, and, therefore, is not limiting.

One difference of the injector 110 over the embodiment of FIGS. 1-5, pertains to the configuration of the activation button assembly 120 and the assembly of the biasing member 122. As shown in FIG. 6, the biasing member, e.g., spring, 122 is mounted within the activation button assembly 120 in the stored energy state thereof, when the activation button assembly is in the unactuated position. The first arm 132 of the activation button assembly 120 includes a lip 132b laterally extending therefrom in a direction opposite the direction of the flange 132a. The spring 122 abuts the underside of the top surface 120b of the activation button assembly 120 at one end and engages the lip 132b at the opposing end when the actuation button assembly is in the unactuated position thereof.

The flange 132a interacts with the elongate first post 124 in a similar manner as described with respect to the embodiment of FIGS. 1-5. In the unactuated position of the activation button assembly 120 (FIG. 6), the lip 132b catches the spring 122 and maintains the spring 122 in the energy storing state. The flange 132a is engaged with the inclined surface 128c of the first post 124, slightly deflecting the first arm 132 laterally in the direction of the lip 132b. Depressing the activation button assembly 120 slides the flange 132a down the inclined surface 128c of the post 124, further deflecting the first arm 132 laterally in the direction of the lip 132b, i.e., toward the spring 122. Such deflection of the first arm 132 maintains the engagement of the spring 122 with the lip 132b. Such deflection of the first arm 132 (by depressing the activation button assembly 120) also stores potential energy in the first arm 132 to straighten back out, thereby sliding back up the inclined surface 128c of the first post 124 and returning the activation button assembly 120 to the unactuated position thereof if the first arm 132 does not travel past the threshold point.

Movement of the activation button assembly 120 sufficiently such that the flange 132a of the first arm 132 surpasses the vertex 130, i.e., the threshold point, triggers retraction of the deflected first arm 132 back toward a substantially undeflected state thereof, hooking/snapping the flanged terminal end 132a thereof into engagement with the undercut 128b of the first post 124 and securing the activation button assembly 120 in the actuated position thereof (FIG. 7). Retraction of the deflected first arm 132 back toward a substantially undeflected state thereof, upon movement of the flange 132a beyond the vertex 130, also engages the flange 132a with the second post 126 and deflects the second post 126 to release the needle hub 116. Return of the first arm 132 into a substantially undeflected configuration thereof also releases the lip 132b from the spring 122. As shown in FIG. 7, the spring 122 is released into the energy releasing state to engage and drive the released needle hub 116 and the injection needle 118 from the retracted position thereof to the injection position thereof.

It will be appreciated by those skilled in the art that changes could be made to the embodiments described above without departing from the broad inventive concept thereof. For example, without limitation, a cam or detent mechanism may alternatively be utilized with the activation button assembly to define a threshold point along the pathway thereof, rather than the inclined surface. Likewise, for example, various needle driving mechanisms may be implemented, such an electrical switch activated needle driving mechanism. It is understood, therefore, that this disclosure is not limited to the particular embodiments disclosed, but it is intended to cover modifications within the spirit and scope of the present disclosure, as set forth in the appended claims.

We claim:

1. A wearable injector comprising:
   an injector housing comprising a base surface and a top surface that opposes the base surface, the base surface being configured to contact a skin surface of a user and having an opening therein, and the top surface defining an opening therethrough;
   an injection needle mounted within the injector housing and translatable along a needle axis between a retracted position, wherein at least a tip of the injection needle is contained within the injector housing, and an injection position, wherein at least the tip of the injection needle protrudes from the injector housing through the opening in the base surface;
   an activation button assembly movably mounted to the injector housing and operatively connected to the injection needle, the activation button assembly being translatable along a button axis, parallel to the needle axis, from an unactuated position to an actuated position, an external surface of the activation button assembly being depressed below the top surface of the injector housing in the actuated position; and
   a biasing member comprising a first end, a second end, and a body that extends between the first end and the second end, the first end of the biasing member being connected with the activation button assembly and the second end of the biasing member being connected to the injection needle, the biasing member being stabilized in a stored energy state in the unactuated position of the activation button assembly, and released in the actuated position of the activation button assembly into an energy releasing state to drive the injection needle along the needle axis from the retracted position thereof to the injection position thereof,
   wherein:
      a position of the activation button assembly between the unactuated position thereof and the actuated position thereof defines a threshold point,
      in the stored energy state, the biasing member biases the activation button assembly into the unactuated position thereof and returns the activation button assembly to the unactuated position in response to movement of the activation button assembly short of the threshold point, and
      movement of the activation button assembly beyond the threshold point secures the activation button assembly in the actuated position.

2. The wearable injector of claim 1, wherein the activation button assembly is depressible along the button axis, and wherein the activation button assembly is depressed in the actuated position relative to the unactuated position.

3. The wearable injector of claim 1, wherein a top surface of the activation button assembly is generally flush with an external surface of the injector housing in the unactuated position of the activation button assembly, and wherein the activation button assembly is secured in the actuated position thereof wherein the top surface of the activation button assembly is depressed from the external surface of the injector housing.

4. The wearable injector of claim 1, wherein the biasing member biases the activation button assembly into the unactuated position thereof.

5. The wearable injector of claim 4, wherein the biasing member returns the activation button assembly to the unactuated position thereof in response to movement of the activation button assembly not surpassing the threshold point.

6. The wearable injector of claim 1, wherein release of the biasing member into the energy releasing state to drive the injection needle from the retracted position thereof to the injection position thereof is triggered solely upon movement of the activation button assembly beyond the threshold point.

7. The wearable injector of claim 6, further comprising a needle hub movably mounted within the injector housing, the injection needle being supported by the needle hub, and the needle hub and the injection needle being translatable between the retracted position and the injection position.

8. The wearable injector of claim 7, wherein the biasing member comprises a spring, the spring being compressed into an at least partially contracted configuration in the stored energy state.

9. The wearable injector of claim 7, further comprising:
   an elongate first post connected with the injector housing and projecting upwardly therefrom, the elongate first post having an upper end comprising a downwardly inclined surface and an undercut underlying the downwardly inclined surface; and
   the activation button assembly comprises a downwardly projecting first arm having a flanged terminal end slidable along the downwardly inclined surface of the elongate first post, the downwardly projecting first arm being elastically deflectable from an original state thereof,
   wherein movement of the activation button assembly along the button axis slides the flanged terminal end of the downwardly projecting first arm along the downwardly inclined surface of the elongate first post, thereby elastically deflecting the downwardly projecting first arm away from the original state thereof.

10. The wearable injector of claim 9, wherein the downwardly inclined surface and the undercut of the elongate first post meet at a vertex defining the threshold point.

11. The wearable injector of claim 10, wherein movement of the activation button assembly beyond the vertex triggers retraction of the first arm back toward the original state thereof, hooking the flanged terminal end thereof onto the undercut of the elongate first post and securing the activation button assembly in the actuated position thereof.

12. The wearable injector of claim 11, further comprising a deflectable second post connected with the injector housing and projecting upwardly therefrom, the deflectable second post including a flange supporting a portion of the needle hub thereon, thereby securing the needle hub and the injection needle in the retracted position thereof.

13. The wearable injector of claim 12, wherein the movement of the activation button assembly beyond the vertex, triggering retraction of the downwardly projecting first arm back toward the original state thereof, engages the flanged terminal end of the downwardly projecting first arm with the deflectable second post and deflects the deflectable second post, whereby the deflected second post releases the needle hub, and, in turn, releases the biasing member into the energy releasing state to drive the needle hub and the injection needle from the retracted position thereof to the injection position thereof.

14. A wearable injector comprising:
an injector housing comprising a base surface and a top surface that opposes the base surface, the base surface being configured to contact a skin surface of a user and having an opening therein, and the top surface defining an opening therethrough;
an injection needle mounted within the injector housing and translatable along a needle axis between a retracted position, wherein at least a tip of the injection needle is contained within the injector housing, and an injection position, wherein at least the tip of the injection needle protrudes from the injector housing through the opening in the base surface;
an activation button assembly movably mounted to the injector housing and operatively connected to the injection needle, the activation button assembly being translatable along a button axis, parallel to the needle axis, from an unactuated position to an actuated position, an external surface of the activation button assembly being depressed below the top surface of the injector housing in the actuated position; and
a biasing member comprising a first end, a second end, and a body that extends between the first end and the second end, the first end of the biasing member being connected with the activation button assembly and the second end of the biasing member being connected to the injection needle, the biasing member being stabilized in a stored energy state in the unactuated position of the activation button assembly, and released in the actuated position of the activation button assembly into an energy releasing state to drive the injection needle along the needle axis from the retracted position thereof to the injection position thereof, wherein:
a position of the activation button assembly between the unactuated position thereof and the actuated position thereof defines a threshold point,
in the stored energy state, the biasing member biases the activation button assembly into the unactuated position thereof and returns the activation button assembly to the unactuated position in response to movement of the activation button assembly short of the threshold point, and
release of the biasing member into the energy releasing state to drive the injection needle from the retracted position thereof to the injection position thereof is triggered solely upon movement of the activation button assembly beyond the threshold point.

15. The wearable injector of claim 14, wherein the biasing member comprises at least one of a spring, an elastic band, or an actuator.

16. The wearable injector of claim 14, wherein the needle axis is offset from the tip of the injection needle and the biasing member extends longitudinally along the needle axis.

17. The wearable injector of claim 14, wherein the biasing member is offset from a center of the activation button assembly.

18. The wearable injector of claim 1, wherein the biasing member comprises at least one of a spring, an elastic band, or an actuator.

19. The wearable injector of claim 1, wherein the needle axis is offset from the tip of the injection needle and the biasing member extends longitudinally along the needle axis.

20. The wearable injector of claim 1, wherein the biasing member is offset from a center of the activation button assembly.

* * * * *